United States Patent
Seibel et al.

(10) Patent No.: US 7,311,723 B2
(45) Date of Patent: Dec. 25, 2007

(54) SCANNING LASER DEVICE AND METHODS OF USE

(75) Inventors: Eric J. Seibel, Seattle, WA (US); Thomas A. Reh, Seattle, WA (US); Blake Miller, Seattle, WA (US)

(73) Assignee: University of Washington, Seattle, WA (US)

( * ) Notice: Subject to any disclaimer, the term of this patent is extended or adjusted under 35 U.S.C. 154(b) by 106 days.

(21) Appl. No.: 10/888,428

(22) Filed: Jul. 9, 2004

(65) Prior Publication Data

US 2005/0015120 A1  Jan. 20, 2005

Related U.S. Application Data

(60) Provisional application No. 60/486,623, filed on Jul. 11, 2003.

(51) Int. Cl.
*A61N 5/067* (2006.01)
(52) U.S. Cl. .................... 607/89; 128/898; 607/88
(58) Field of Classification Search ............... 128/898; 607/88–94
See application file for complete search history.

(56) References Cited

U.S. PATENT DOCUMENTS

| | | | | |
|---|---|---|---|---|
| 5,109,844 A * | 5/1992 | de Juan et al. ............. 607/53 |
| 5,159,927 A * | 11/1992 | Schmid .................... 607/53 |
| 5,653,751 A * | 8/1997 | Samiy et al. ............ 623/6.63 |
| 5,659,327 A * | 8/1997 | Furness et al. ............. 345/8 |
| 5,709,645 A * | 1/1998 | Siever .................... 600/27 |
| 5,895,415 A * | 4/1999 | Chow et al. ............... 607/54 |
| 6,350,275 B1 * | 2/2002 | Vreman et al. ............ 607/88 |
| 6,400,989 B1 * | 6/2002 | Eckmiller ................. 607/54 |
| 6,474,816 B2 * | 11/2002 | Butler et al. ............. 351/221 |
| 6,976,998 B2 * | 12/2005 | Rizzo et al. ............ 623/6.63 |
| 7,003,355 B1 * | 2/2006 | Suaning et al. ............ 607/54 |
| 2002/0042638 A1 | 4/2002 | Iezzi et al. |
| 2002/0087202 A1 * | 7/2002 | Chow et al. ............... 607/53 |
| 2002/0101568 A1 * | 8/2002 | Eberl et al. ............. 351/211 |
| 2003/0004418 A1 | 1/2003 | Marmorstein |
| 2003/0181957 A1 * | 9/2003 | Greenberg et al. ......... 607/54 |
| 2004/0030383 A1 * | 2/2004 | Havey et al. ............ 623/4.1 |
| 2004/0075812 A1 * | 4/2004 | Kardon et al. .......... 351/206 |

(Continued)

OTHER PUBLICATIONS

"DataGlass2/A," Specification Sheet, Shimadzu Precision Instruments, Inc., Phoenix, Arizona, 1 page, mid-Jul. 2004.

(Continued)

*Primary Examiner*—Henry M Johnson, III
(74) *Attorney, Agent, or Firm*—Christensen O'Connor Johnson Kindness PLLC

(57) ABSTRACT

In one aspect, the invention provides vision prosthesis systems. Exemplary vision prosthesis systems of the invention comprise a light energy generator operably connected to a wearable head piece comprising a device for directing light energy produced by the light energy generator onto a mammalian retina, wherein the light energy generator is tuned to emit light energy of sufficient power to modulate neural activity in the retina. In another aspect, the invention provides methods for irradiating neurons in the retina of the mammalian eye by directing light energy produced by a light energy generator onto a mammalian retina. The methods of the invention may be used to directly modulate the activity of retinal neurons or to introduce molecules into retinal cells.

18 Claims, 6 Drawing Sheets

U.S. PATENT DOCUMENTS

2004/0088026 A1* 5/2004 Chow et al. .................. 607/54
2004/0215293 A1* 10/2004 Eells et al. .................... 607/89

OTHER PUBLICATIONS

"Fiber Collimators," *Diode Laser Modules and Instruments*, Micro Laser Systems, Garden Grove, Calif., 2 pages, ca 1999.

"High Performance UV to Blue Diode Lasers," *Diode Laser Modules and Instruments*, Micro Laser Systems, Garden Grove, Calif., 2 pages, ca 1999.

"OEM Drivers," *Diode Laser Modules and Instruments*, Micro Laser Systems, Garden Grove, Calif., 2 pages, ca 1999.

"UV to Blue Diode Lasers," *Diode Laser Modules and Instruments*, Micro Laser Systems, Garden Grove, Calif., 2 pages, ca 1999.

Callaway, E.M., and R. Yuste, "Stimulating Neurons With Light," *Current Opinion in Neurobiology 12*:587-592, published online Oct. 1, 2002.

Cao, X.A., et al., "Blue and Near-Ultraviolet Light-Emitting Diodes on Free-Standing GaN Substrates," *American Institute of Physics Web Site*, © 2004, <http://apl.aip.org> [retrieved Nov. 3, 2004], and *App. Phys. Letters 84*(21):4313-4315, May 24, 2004.

Denk, W., and P.B. Detwiler, "Optical Recording of Light-Evoked Calcium Signals in the Functionally Intact Retina," JSTOR.org, © 2000-2004, <http://links.jstor.org/sici?sici=0027-8424%2819990608%2996%3A12%3C7035%3AOROLCS%3E2.0.CO%3B2-F> [retrieved Jan. 21, 2004], and *Proc. Nat. Acad. Sci. 96*(12):7035-7040, Jun. 8, 1999.

Denk, W., et al., "Two-Photon Laser Scanning Fluorescence Microscopy," JSTOR.org, © 2000-2004, <http://links.jstor.org/sici?sici=0036-8075%2819900406%293%3A248%3A4951%3C73%3ATLSFM%3E2.0.CO%3B2-0> [retrieved Jan. 13, 2004], and *Science 248*(4951):73-76, Apr. 6, 1990.

Dillon, J., et al., "Transmission Spectra of Light to the Mammalian Retina," *Photochem. and Photobiol.* 71(2):225-229, 2000.

Helmchen, F., et al., "A Miniature Head-Mounted Two-Photon Microscope: High-Resolution Brain Imaging in Freely Moving Animals," *Neuron 31*:903-912, Sep. 27, 2001.

Hirase, H., et al., "Multiphoton Stimulation of Neurons," *J. Neurobiology 51*(3):237-247, Jun. 5, 2002.

Kelly, J.P., et al., "Vision With a Scanning Laser Display: Comparison of Flicker Sensitivity to a CRT," *Displays 22*:169-175, 2001.

Kleweno, C.P., et al., "The Virtual Retinal Display as a Low-Vision Computer Interface: A Pilot Study," *J. Rehab. Res. and Dev.* 38(4):431-442, Jul./Aug. 2001.

König, K., "Multiphoton Microscopy in Life Sciences," *J. Microscopy 200*(Part 2):83-104, Nov. 2000.

König, K., et al., "Optical Gene Transfer by Femtosecond Laser Pulses," *Proceedings of SPIE* vol. 4963, San Jose, California, Jan. 26-28, 2003, pp. 81-88.

Lee, C.M., et al., "Efficient Image Segmentation of Walking Hazards Using IR Illumination in Wearable Low Vision Aids," *Proceedings of the 6th International Symposium on Wearable Computers*, Seattle, Washington, Oct. 7-10, 2002, pp. 127-128.

Letter of Response to Request Concerning "New UV & Blue Diode Lasers," et al., Micro Laser Systems, Garden Grove, Calif., 1 page, Jul. 2004.

Lozovoy, V.V., et al., "Multiphoton Intrapulse Interference. II. Control of Two- and Three-Photon Laser Induced Fluorescence With Shaped Pulses," *American Institute of Physics Web Site*, © 2003, <http://ojps.aip.org/jcpo/jcpcr> [retrieved Jan. 22, 2004], and *J. Chem. Physics 118*(7):3187-3196, Feb. 15, 2003.

Ouzounov, D.G., et al., "Delivery of Nanojoule Femtosecond Pulses Through Large-Core Microstructured Fibers," *Optics Letters 27*(17):1513-1515, Sep. 1, 2002.

Palumbo, G., et al., "Targeted Gene Transfer in Eucaryotic Cells by Dye-Assisted Laser Optoporation," *J. of Photochem. and Photobiol.* 36:41-46, 1996.

Paterson, L., et al., Photoporation and Cell Transfection Using a Violet Diode Laser, *Optics Express 13*(2):595-600, Jan. 24, 2005.

Schneckenburger, H., et al., "Laser-Assisted Optoporation of Single Cells," *J. Biomed. Optics 7*(3):410-416, Jul. 2002.

Seibel, E.J. and Q.Y.J. Smithwick, "Unique Features of Optical Scanning, Single Fiber Endoscopy," *Lasers in Surgery and Medicine 30*:177-183, 2002.

Seibel, E.J., et al., "P-37: Optical Fiber Scanning as a Microdisplay Source for a Wearable Low Vision Aid," Society for Information Display, May 19-24, 2002, Boston, *SID 02 Digest*, pp. 1-4.

So, P.T.C., et al., "Two-Photon Excitation Fluorescence Microscopy," *Annu. Rev. Biomed. Eng.* 2:399-429, 2000.

Soughayer, J.S., et al., "Characterization of Cellular Optoporation With Distance," *Anal. Chem.* 72(6):1342-1347, Mar. 15, 2000.

Tao, W., et al., "Direct Gene Transfer Into Human Cultured Cells Facilitated by Laser Micropuncture of the Cell Membrane," JSTOR.org, © 2004, <http://links.jstor.org/sici?sici=0027-8424%2819870615%2984%3A12%3C4180%3ADGTIHC%3E2.0.CO%3B2-D> [retrieved Jan. 15, 2004], and *Proceedings of the National Academy of Sciences of the United States of America 84*(12):4180-4184, Jun. 15, 1987.

Theer, P., et al., "Two-Photon Imaging to a Depth of 1000 μm in Living Brains by Use of a Ti:Al$_2$O$_3$ Regenerative Amplifier," *Optics Letters 28*(12):1022-1024, Jun. 15, 2003.

Thomas, R.J., et al., "A Comparative Study of Retinal Effects From Continuous Wave and Femtosecond Mode-Locked Lasers," *Lasers in Surgery and Medicine 31*:9-17, 2002.

Tirlapur, U.K. and K. König, "Targeted Transfection by Femtosecond Laser," *Nature 418*:290-291, Jul. 18, 2002.

Viirre, E., et al., "Laser Safety Analysis of a Retinal Scanning Display System," *J. Laser App.* 9:253-260, 1997.

Zeira, E., et al., "Femtosecond Infrared Laser—An Efficient and Safe in Vivo Gene Delivery System for Prolonged Expression," *Mol. Therapy 8*(2):342-350, Aug. 2003.

\* cited by examiner

SCANNING LASER DEVICE AND METHODS OF USE

CROSS-REFERENCE TO RELATED APPLICATION

This application claims the benefit of U.S. Provisional Application No. 60/486,623, filed Jul. 11, 2003, under 35 U.S.C. § 119.

STATEMENT OF GOVERNMENT LICENSE RIGHTS

This invention was made with government support under 9978888 awarded by the National Science Foundation. The government has certain rights in the invention.

FIELD OF THE INVENTION

The present invention relates to methods and prosthetic apparatus for modulating neural activity and in particular to apparatus for producing an artificially-formed sense, such as vision.

BACKGROUND OF THE INVENTION

The mammalian eye includes a cornea, a fluid-filled anterior chamber, a lens, a fluid-filled posterior chamber, and a photosensitive retina. The designations "anterior" and "posterior" are with reference to the lens. Light enters the eye through the cornea, passes through the anterior chamber and is focused onto the retina by the lens. The retina is composed of numerous types of cells including photosensitive rods, that are responsible for night vision, and photosensitive cones that are responsible for high acuity day vision. The rods and cones communicate with neurons in the retina that transmit nerve impulses to the visual centers of the brain where this information is processed to generate the perception of visual information. For example, rods and cones communicate with bipolar cells, that, in turn, communicate with ganglion cells that transmit nerve impulses to the brain.

Half of all blindness is caused by damage or disease of the retina (Zrenner (2002) *Science* 295(5557):1022-26). Death of photoreceptors has many causes, some of which are the results of known, underlying, genetic mutations, while others are of unknown cause. In the condition known as retinitis pigmentosa, the rods degenerate first and result in loss of night vision, and later the cones degenerate, resulting in total blindness. In the condition known as age-related macular degeneration, the cones degenerate, and since they are necessary for high acuity vision, these individuals also become functionally blind. In both diseases the non-photoreceptive neurons, such as the bipolar and ganglion cells, remain largely intact (Santos et al. (1997) *Arch. Ophthamol.* 115:511-5; Kim et al. (2002) *Retina* 22:464-70; Kim et al. (2002) *Retina* 22:471-7). Due to the many applications of lasers and the increasing use in the military, laser eye injuries that destroy the retinal pigmented epithelium and light-sensitive photoreceptors are a growing problem (Barkana & Belkin (2000) *Surv. Ophthalmol.* 44(6):459-478). The retinal pigmented epithelium is located between the photoreceptors and the choroid of the eye. Certain laser eye injuries preserve the functionality of the retinal neurons, so that the use of vision prostheses become a viable option (e.g., krypton laser damage, Weiland et al. (1999) *Graefe's Arch. Clin. Exp. Ophthalmol.* 237:1007-13).

There are currently no treatments for most eye injuries and diseases that cause the destruction and degeneration of photoreceptors. There have been attempts, however, to develop a retinal prosthesis by the implantation of multiple active electrodes which sense light impinging on the retina and generate corresponding electrical signals that stimulate the healthy retinal neurons in the eye (see, e.g., Dagnelie & Massof (1996) *IEEE Spectrum*, May 22-29; Chase (1999) *Technol. Rev.* 102:44-48; Haystead (1999) *Vision Systems Design* 4(6):31-36; Chow et al. (2002) *J. Rehab. Res. Dev.* 39(3):313-22; Humayun et al. (2003) *Vision Res.* 43(24): 2573-81). Implanted electrode arrays have significant limitations, however, such as power dissipation, incompatibility with surrounding biological tissues, low density of photocells in the electrode arrays, and the lack of knowledge about the neural interconnections to the bipolar and ganglion cells, and the type of stimulation required to mimic retinal signal processing (Liu et al. (2000) *IEEE J. Solid-State Circuits*, 35(10):1487-1497; Zrenner (2002) *Science* 295(5557):1022-26).

Thus, there is a continuing need for less invasive prosthetic devices capable of stimulating, inhibiting, or otherwise modulating, the activity of retinal neurons, in damaged and diseased retinas in which the photosensitive cells are functionally impaired, in order to generate a pattern of nerve impulses that are transmitted to the visual centers of the brain to yield visual information. There is also a need for manipulating the mammalian retina to promote health, for example, by stimulating retinal cells to take up molecules such as nucleic acids, proteins, and nutrients.

SUMMARY OF THE INVENTION

In one aspect, the invention provides vision prosthesis systems. Exemplary vision prosthesis systems of the invention comprise a light energy generator operably connected to a wearable head piece comprising a device for directing light energy produced by the light energy generator onto a mammalian retina, wherein the light energy generator is tuned to emit light energy of sufficient power to modulate neural activity in the retina. The light energy generator may be tuned to emit infrared, visible, or ultraviolet light energy. For light energy between about 400 and 700 nm wavelengths, the power of the light energy is generally greater than about 1 mW. In some embodiments, the light energy generator is tuned to emit pulses of light energy. The light energy generator may be selected from the group consisting of a laser, a laser diode, a mercury arc lamp, and a light-emitting diode. In some embodiments, the light energy generator is a femtosecond-pulsed infrared laser or a picosecond-pulsed infrared laser.

The device for directing light energy onto the mammalian retina may be a scanner. Suitable scanners for use in the systems of the invention include, but are not limited to, fiber optic scanners, mirror scanners, and acousto-optical deflectors. In some embodiments, the device for directing light energy onto the retina is a non-resonant scanner.

The systems of the invention may further comprise an image source, for example, a camera, operably connected to the image processor. In some embodiments, the systems of the invention are controlled by a computer.

In some embodiments, the invention provides a vision prosthesis system, comprising:

a light energy generator tuned to emit light energy of sufficient power to modulate neural activity in the retina, wherein the power level of light energy emitted between about 400 and 700 nm wavelengths is greater than about 1 mW;

a wearable head piece comprising a scanner and an ocular lens, wherein the scanner is operably connected to the light energy generator and configured for scanning light energy produced by the light energy generator onto a mammalian retina, and wherein the ocular lens is operably connected to the scanner for focusing the light energy onto the retina; and an image processor operably connected to an image source and configured to transmit electrical signals corresponding to an image to the scanner.

A further embodiment of a visual prosthesis system of the invention comprises a wearable head piece comprising a non-resonant scanner operably connected to a light energy generator, wherein the light energy generator is tuned to emit light energy of sufficient power to directly modulate the activity of neurons in a mammalian retina and wherein the scanner is configured for scanning the light energy onto the mammalian retina.

Another aspect of the invention provides methods for irradiating neurons in the retina of the mammalian eye. In some embodiments, the methods of the invention comprise the step of directing light energy onto a mammalian retina using a visual prosthesis system to directly modulate the activity of a retinal neuron, the visual prosthesis system comprising a light energy generator operably connected to a wearable head piece comprising a device for directing light energy produced by the light energy generator onto a mammalian retina, wherein the light energy generator is tuned to emit light energy of sufficient power to modulate neural activity in the retina. Some embodiments provide methods modulating neural activity in the retina of a mammalian eye, comprising the step of directing light energy produced by a light energy generator onto a mammalian retina to directly modulate the activity of retinal neurons. Further embodiments provide methods for introducing a molecule into a retinal cell in vivo, comprising the step of directing light energy produced by a light energy generator onto a mammalian retina in vivo, wherein the retinal cell comprises a plasma membrane and the light energy has a power sufficient to permeabilize the plasma membrane, thereby allowing a molecule outside the retinal cell to enter the retinal cell. The methods for introducing a molecule into a retinal cell in vivo may comprise the steps of (a) contacting a cell having a plasma membrane in a mammalian retina with a molecule in vivo; and (b) directing light energy produced by a light energy generator onto the mammalian retina, wherein the light energy has sufficient power to permeabilize the membrane of the contacted cell in the mammalian retina, thereby allowing the molecule to enter the cell. Exemplary molecules for optoporating into retinal cells include, but are not limited to, nutrient molecules, proteins, nucleic acids, and lipids.

The light energy used in the methods of the invention may be produced by a light energy generator selected from the group consisting of a laser, a laser diode, a mercury arc lamp, and a light-emitting diode. For example, the light energy may be produced by a femtosecond-pulsed infrared laser or a picosecond-pulsed infrared laser.

In some embodiments, the light energy is directed onto the retina using a scanner. For example, light energy may be scanned onto the retina in raster format or in vector graphics format. In some embodiments of the methods of the invention the eye comprises an artificial lens to focus the light energy onto the retina.

The systems and methods of the invention are useful, for example for modulating the activity of neurons in damaged or diseased retinas in which the photosensitive cells are functionally impaired in order to generate a visual image. Another exemplary use for the methods of the invention is for introducing molecules into retinal cells in order to promote the health and survival of the retina.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
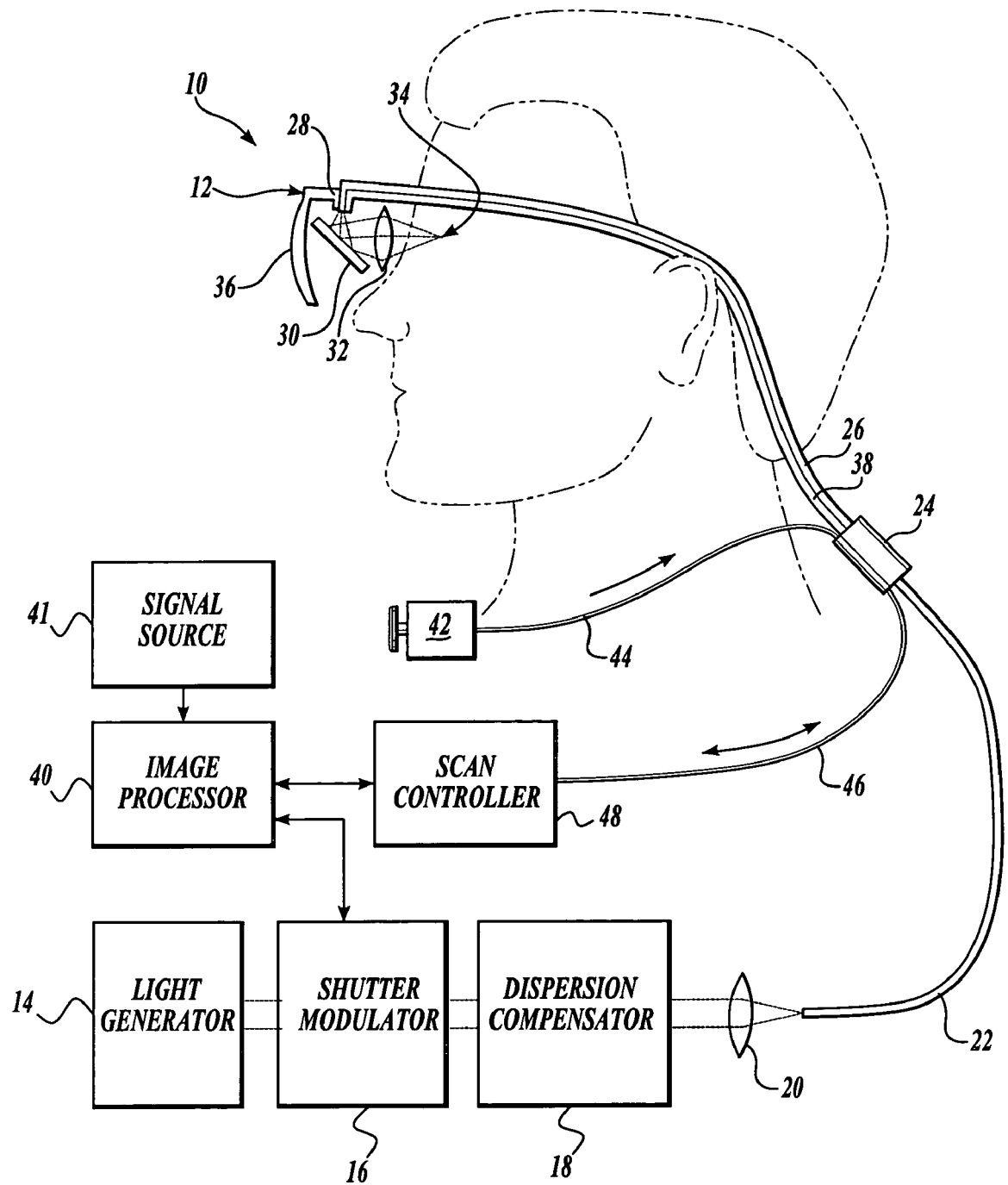
FIG. 1 depicts one exemplary embodiment of a system for practicing femtosecond-pulsed to picosecond-pulsed near-infrared laser excitation according to the present invention.

In one aspect, the present invention provides a vision prosthetic system that directly modulates neural activity in the retina of a mammalian eye, such as a human eye. The prosthetic system is configured to irradiate the retina of a mammalian eye with light energy. In some embodiments, the vision prosthesis system comprises a light energy generator operably connected to a wearable head piece comprising a device for directing light energy produced by the light energy generator onto a mammalian retina, wherein the light energy generator is tuned to emit light energy of sufficient power to modulate neural activity in the retina.

As used herein, the term "light energy" includes infrared (IR), visible and ultraviolet (UV) light energy. Thus, the wavelengths of the light energy may be the in the range of about 300 nm to about 1800 nm. Exemplary power levels applicable to light energy of wavelengths between about 300 nm and about 1800 nm are between about 2 mW and about 500 mW. For light energy with a wavelength between about 400 and 700 nm, the power level entering the eye is generally greater than about 1 mW. A power level in the range of 1 mW is much higher than the maximum permissible exposure limits for long-term viewing of a stationary laser beam within the visible spectrum. Typically, individual cells within the retina are exposed to less than 1 second duration of continuous light exposure. In some embodiment, the light energy is pulsed. Pulsing the light energy may increase the peak power of the light energy generator and may also reduce heating of the retina. For example, the light energy may be pulsed while the beam entering the eye is not scanning. In other embodiments the pulsed or continuous-wave light energy is scanned across the retina, thereby limiting the exposure time of individual cells within the retina.

The light energy is directed onto the neuronal layer of a mammalian retina by a device suitable for the delivery of the light energy to the retina (e.g., a scanner) and the focusing ability of the natural optics of the eye and, optionally, corrective optics. At the focal point of the light energy beam, the retinal neuron responds to the focused illumination resulting in a modulation of neural activity. The term "modulating neural activity in the retina" encompasses any change in the frequency, intensity, and/or pattern of nerve impulses in any type of neuron (e.g., bipolar cells and ganglion cells) in the retina. For example, the frequency of nerve impulses in one or more types of neurons in the retina of a mammalian eye can be increased or decreased by treating the retinal neurons in accordance with the methods of the present invention. According to the invention, the modulation of neural activity in the retina can occur directly, that is, in the absence of photochemical signal transduction mediated by photoreceptors.

In another aspect, the invention provides methods for irradiating neurons in the retina of a mammalian eye, comprising the step of directing light energy onto a mammalian retina using a visual prosthesis system, the visual prosthesis system comprising a light energy generator operably connected to a wearable head piece comprising a device for directing light energy produced by the light energy generator onto a mammalian retina. In some embodiments, the light energy generator is tuned to emit short pulses of light energy of wavelengths between about 700 nm and about 1100 nm (the NIR 'optical window' range where absorption within human tissue is a minimum). In some embodiments, the power level of the light energy emitted by the NIR light energy generator is between about 2 mW and about 500 mW.

Some embodiments of the invention provide methods for modulating neural activity in the retina of a mammal, wherein the methods each comprise the step of directing light energy produced by a light energy generator (e.g., laser light energy) onto a mammalian retina to directly modulate neural activity in the retina. Thus, the light energy generator is tuned to emit light energy of sufficient power to modulate neural activity in the retina. The modulation of neural activity in the retina may generate the sensation of vision in the mammal. The irradiated retina does not include exogenous (i.e., introduced into the retina by artificial means) photoactivatable precursor molecules that are activated by light to release a neuroactive molecule that interacts with a neural cell in the retina, thereby modulating activity of the neural cell. The methods of the present invention rely, instead, on the direct interaction of light with neural cells in the retina in the absence of photochemical signal transduction mediated by photoreceptors. While not wishing to be bound by theory, it is hypothesized that sufficiently energetic light waves causes the temporary formation of pores in the cell membrane of neural cells, thereby resulting in membrane depolarization and the generation of action potentials that transmit nerve signals to the visual cortex of the mammalian brain thereby generating a visual image. An alternative mechanism for the modulation of neural activity may be that light changes the electric field across the cell membrane, thereby depolarizing or hyperpolarizing the cell (Hirase et al. (2002) *J. Neurobiol.* 51:237-47).

In further embodiments, the invention provides methods for introducing molecules into retinal cells in vivo by optoporation. In some embodiments, the methods comprise the step of directing light energy produced by a light energy generator onto a mammalian retina in vivo, wherein the retinal cell comprises a plasma membrane and the light energy has an intensity sufficient to permeabilize the membrane of a retinal cell, thereby allowing a molecule outside the retinal cell to enter the retinal cell. The molecule outside the retinal cell may be an endogenous molecule, such as a nutrient molecule. In some embodiments, the methods comprise the steps of: (a) contacting a cell in a mammalian retina with a molecule in vivo; and (b) directing light energy produced by a pulsed light energy generator onto the mammalian retina, wherein the light energy has an intensity sufficient to temporarily permeabilize the membrane of the contacted cell in the mammalian retina, thereby allowing the molecule to enter the cell. Exemplary molecules useful for optoporation into retinal cells include nutrient molecules, proteins, nucleic acids, lipids, etc. For example, the methods may be used to optoporate nucleic acid molecules encoding a protein, as described in EXAMPLE 1. Other suitable nucleic acids for optoporation into retinal cells include, but are not limited to, antisense RNA, small-interfering RNA, and modified nucleic acids.

In some embodiments, the optoporation methods of the invention are used to introduce molecules that promote the survival of the retinal cells and prevent further degeneration in the diseased retina. Exemplary molecules that are suitable for promoting survival and preventing degeneration of the retina include, but are not limited to, growth factors or nucleic acid molecules coding for growth factors, such as neurotrophins (e.g., Nerve Growth Factor, NGF, Brain Derived Neurotrophic Factor, BDNF, Neurotrophin-3, NT-3) and small molecules that act directly on second messenger signal transduction cascades downstream of the growth factors, such as TPA to activate the protein kinase C signaling cascade. The optoporation methods of the invention may also be used to introduce molecules that act on the ion channels of the cell from the intracellular side of the plasma membrane, to stimulate the cells to fire action potentials, either through their direct action on the channel, or through the activation of a second messenger cascade, such as cyclic-AMP or cyclic-GMP, which then acts to modulate channel conductance.

Prior to discussing various exemplary embodiments of a prosthetic device constructed according to the invention, it is appropriate to first discuss various biological components of an eye that interact with the light energy delivered by the prosthetic device. Neurons that are located in the retina of a mammalian eye include, but are not limited to, bipolar cells (including ON and OFF subtypes, and rod and cone subtypes), ganglion cells (including ON and OFF subtypes, bistratified subtype, red/green color opponent subtype, and blue/yellow color opponent subtype), horizontal cells and amacrine cells (which include numerous subtypes).

According to the methods of the invention, retinal neural activity is modulated both nondestructively and with minimal-invasiveness by irradiating the retinal neuronal layer with light energy, for example pulses of light energy. Irradiation of the retinal neuronal layers can be achieved by any useful light energy generator. Exemplary light energy generator that are useful in the practice of the present invention include, but are not limited to, lasers, laser diodes, mercury arc lamps, and light-emitting diodes (LEDs). In some embodiments, the light energy generator is a laser, as described in more detail below. Lasers can be tuned to a desired wavelength of light, and can deliver light to the retina at very high resolution and intensity from a single optical fiber. Typically, a single laser is tuned to deliver light at an electromagnetic frequency, duration, power, and repetition rate that is optimal for modulating neural activity. However, two or more lasers tuned at different wavelengths may also be used. Single photon or multi-photon (e.g., two or three photon) excitation may be used (He et al. (2002) *Nature* 415:767-70). Effective three-photon suppression to avoid unwanted high-energy absorption has been demonstrated by phase-controlled multi-photon interference (Lozovoy et al. (2003) *J. Chem. Phys.* 118(7):3187-96), which may be used to selectively excite the s, m, and l cones (color vision). Exemplary ranges for single-photon ultraviolet (UV)-violet excitation include wavelengths between about 300 nm to about 450 nm, such as about 315 nm to about 400 nm or about 325 nm to about 425 nm. Exemplary ranges for multi-photon deep-red to infrared excitation include wavelengths between about 650 nm to about 1800 nm, such as about 650 nm to about 1200 nm wavelengths for two-photon photostimulation or about 900 nm to about 1800 nm for three-photon excitations.

In some embodiments of the present invention, electrical signals (that encode information that represents a visual image) are processed to direct a scanner to scan a beam of light produced by a light source onto the retina, thereby forming a pattern of light intensities on the retina. Exemplary scanners that are suitable for use according to the invention include, but are not limited to, fiber optic scanners, mirror scanners, and acousto-optical deflectors. The scanners may be resonant scanners (e.g., raster scanning) or non-resonant scanners (e.g., vector graphics scanning). Most optical scanners for low-power applications such as visual displays use raster scanning, where the entire field is scanned and both on and off pixels being scanned. However, for applications that require higher optical power per on-pixel, vector graphics scanning or pixel-addressable scanning is desirable. Typically, a resonant scanner cannot be used effectively for a vector graphics scanning, since the scanner mechanism is designed to run at a fixed frequency and a constant scan amplitude, while vector graphics scanners typically operate at various rates and amplitudes.

The light energy is scanned onto the retina to directly modulate the activity of the retinal neurons. The amount of neural activity is proportional to the dose of irradiation delivered. Thus, the pattern of light intensities generates a corresponding pattern of nerve impulses within the retina that are communicated to the brain, which uses this information to construct a mental picture of the visual image (i.e., the brain "sees" the visual image). In some embodiments, the light source generates a beam of light of sufficiently high resolution to generate a visual image that approximates, or equals, the resolution of normal sight.

Thus, in some embodiments, the present invention provides a system for modulating neural activity, particularly in the retina of a mammalian eye, wherein light energy produced by a light energy generator is directed onto the retina in a pattern corresponding to the image to be perceived. In embodiments where a scanner is used to direct the light energy onto the retina, the scanning pattern may be a standard repeating raster pattern or in a scan pattern that follows the outline of the objects to be conveyed to the brain (e.g., vector scanning graphical format).

FIG. 1 illustrates one exemplary embodiment of a system 10 constructed according to the present invention. System 10 includes a wearable headpiece 12 with components, discussed below, capable of directing light energy to the user's retina. Briefly summarized, light energy is emitted from a pulsed light energy generator 14 that passes the light energy through an electronic shutter and modulator 16 to a group velocity dispersion compensator 18. The light energy is focused by a lens 20 and thereafter conducted through a fiber optic cable 22. In the embodiment shown in FIG. 1, fiber optic cable 22 is attached to a cabling disconnect 24, which releasably connects cable 22 to fiber optic cable 26. Fiber optic cable 26 terminates in an optical fiber scanner 28. Light energy emerging from optical fiber scanner 28 is directed via a mirror or beam splitter 30 to an ocular lens 32 that focuses the light energy onto the retina 34 of the user of headpiece 12.

Light energy generator 14 generally includes lasers that provide sub-picosecond pulses of near-infrared (NIR) light that repeat at greater than 50 MHz. Such femtosecond-pulsed lasers have been used for optoporation and more commonly for multi-photon (e.g., two-photon) excitation of dyes and fluorophores. The most common form of these femtosecond-pulsed lasers are the titanium-sapphire laser manufactured by Spectra Physics Inc. (Mountain View, Calif.) and Coherent Inc. (Santa Clara, Calif.). In one example, the lasers may be comprised of these currently available femtosecond-pulsed lasers that produce light energy in the near infrared (NIR) optical spectrum (690-1050 nm). A suitable pulsed laser in one embodiment of the invention may produce a pulse train of 100 femtosecond pulses at a repetition rate of 80 MHz at 790 nm. Light energy generator 14 may include more than one operably linked lasers; for example, a green pump laser may be operably linked to a Ti:Sapphire laser to produce the light energy output. Short NIR pulses of higher peak powers but at lower pulse repetition rates (<1 MHz) can be generated by adding a cavity dumping oscillator to the Ti:Sapphire laser output or having a Ti:Sapphire regenerative amplifier, such as RegA 9000/9050 by Coherent, Santa Clara, Calif. (see Theer et al. (2003) *Optics Lett.* 28(12):1022-4).

Electronic shutter and modulator 16 is controlled by electrical signals from an image processor 40 and serves to modulate the intensity of the beam of light energy communicated to the wearer's retina. Electronic shutter and modulator 16 may also interrupt the light energy produced by pulsed light energy generator 14, thereby producing light and dark areas on the user's retina when the light energy is scanned onto the retina. The electronic shutter may also be used without a modulator, making a binary image without grayscale for the user of the prosthetic device. In one embodiment, electronic shutter and modulator 16 is suitably comprised of an acousto-optical modulator or Pockels Cell.

Group velocity dispersion compensator 18 preconditions the light pulses to compensate for known degradation of the light pulses that occurs as the light pulses are communicated to headpiece 12 and beyond to the retina. Group velocity dispersion compensator 18 may be suitably comprised of optical prisms or diffraction gratings (Fan et al. (1999) *Biophysical J.* 76:2412-2420; Helmchen et al. (2001) *Neuron* 31:903-912). The preconditioned light pulses emerging from group velocity dispersion compensator 18 are directed via lens 20 to optical fiber 22. Optical fiber 22, in one embodiment, is a singlemode optical fiber. Microstructured optical fibers (photonic crystal fibers) have been developed that allow higher power transmission of IR femtosecond-pulsed laser light, eliminating the need for the group velocity dispersion compensation for preservation of femtosecond pulse quality over meters of fiber length (Ouzounov et al. (2002) *CLEO* 2002, 455; Myaing et al. (2003) *Optics Lett.* 28(14):1224-6). These optical fibers are commercially available from Crystal Fibre (Lyngby, Denmark), Blaze Photonics (Bath, England), and OmniGuide Communications Inc. (Cambridge, Mass.).

FIG. 1 depicts an optical fiber scanner 28 that provides two dimensional X-Y scanning of the light energy emerging from headpiece optical fiber 26, thereby producing a two dimensional image on the user's retina. Optical fiber scanner 28 may employ piezoelectric elements that move according to arbitrary voltages applied to the X and Y actuators computer-controlled vector scanning, or move according to fixed voltage and frequency that create resonant X & Y scanner motions for fixed raster scanning. Alternative systems of the invention may suitably use mirror scanning to produce two-dimensional images on the user's retina. In mirror scanning, piezoelectric, electro-magnetic, or electrostatic elements may be used to control the position of a mirror that directs the light energy in both X and Y directions to produce a scanned image. In both optical fiber scanning and mirror scanning, the light energy is used according to the invention to directly modulate retinal neural activity according to the pattern of light across two-dimensions. The spatial pattern of modulated nerve firings will communicate the "image" to the user's brain.

Image processor 40 generates electrical signals that control both electronic shutter and modulator 16 and a scan controller 48. Image processor 40 may be comprised of one or more computer processing elements that internally generate an image signal or receive an image signal from an external source 41, such as a television, computer, digital video disk (DVD) player, etc. In one embodiment, an optional body-mounted camera 42 produces either still or continuous video imagery that is communicated to image processor 40 via wires 44, 46, and scan controller 48. Image processor 40 causes electronic shutter and modulator 16 to output light energy pulses that are scanned onto the user's retina. Image processor 40 controls the scanning of the light pulses by way of drive signals from scan controller 48. Another function of image processor 40 and scan controller 48 is to re-map the pixels from the source, such as a video camera 42 or alternative raster-scanned image source 41 (e.g., television, computer, or DVD player), into a vector graphics format so the delivered neural stimulation is most effective (see FIG. 4).

Scan controller 48 communicates electrical signals to optical fiber scanner 28 via wire 46, which connects through cabling disconnect 24 to wire 38. Wire 38 is, in turn, connected to optical fiber scanner 28. Sensors used to detect scan position of moving optical fiber scanner 28 can be used to reduce scanner-induced distortion in the image. Sensors used to detect when the eye is looking straight ahead can be used to trigger the shutter so the laser excitation is maintained on the same region of the retina.

Wearable headpiece 12 may further include a spectacle lens 36. Lens 36 may suitably provide a cosmetic effect for the user by shielding the components of the system 10 that are disposed behind lens 36. Lens 36 may also be darkened or made reflective to produce a dark environment for the user's eyes. An optional head strap may be used to attach headpiece 12 to the user's head.

Examples of lasers used for pulsed light energy generator 14 may include the MaiTai or Millennium and Tsunami models of Ti-Sapphire lasers manufactured by Spectra Physics of Mountain View, Calif. or the Mira and Chameleon models manufactured by Coherent of Santa Clara, Calif. Recently, diode-based, femtosecond-pulsed NIR laser systems have become available that are much smaller in size and lower in cost compared to the standard Ti-sapphire laser systems identified above (Hogan, *Biophotonics Intl.* May 2003, p. 42-7). Diode-based, single IR wavelength femtosecond-pulsed lasers have been engineered to be battery-powered, small, and portable (Agate et al. (2000) *Optics Comm.* 205:207-13). Therefore, the embodiment that uses femtosecond-pulsed NIR lasers may be useful in embodiments of the present invention that are completely wearable and portable.

Lasers currently contemplated for the embodiment shown in FIG. 1 produce light energy in pulsed beams that may be transmitted at lower power through the eye. The photons in each of the light beams are directed or focused in system 10 to produce a high-intensity spot, on the user's retina, of high enough power density to directly activate the neurons. An advantage of this embodiment of the invention is that each of the light beams does not have sufficient power density or intensity to photostimulate receptors in the user's eye until the beams are focused on a particular spot. This means that surrounding ocular tissue and neurons in the user's eye are not activated by the beams, thereby producing higher contrast in the stimulated image than using photostimulation based on linear, single-photon processes. The major absorber of light in the diseased eye is the retinal pigmented epithelium that contains melanin. Melanin has maximal absorbance at 500 nm and significantly less, possibly negligible, absorption in the near infra-red (>700 nm) for single-photon absorption, see Roderick (1973) *The Vertebrate Retina*, page 182).

Figure 2:
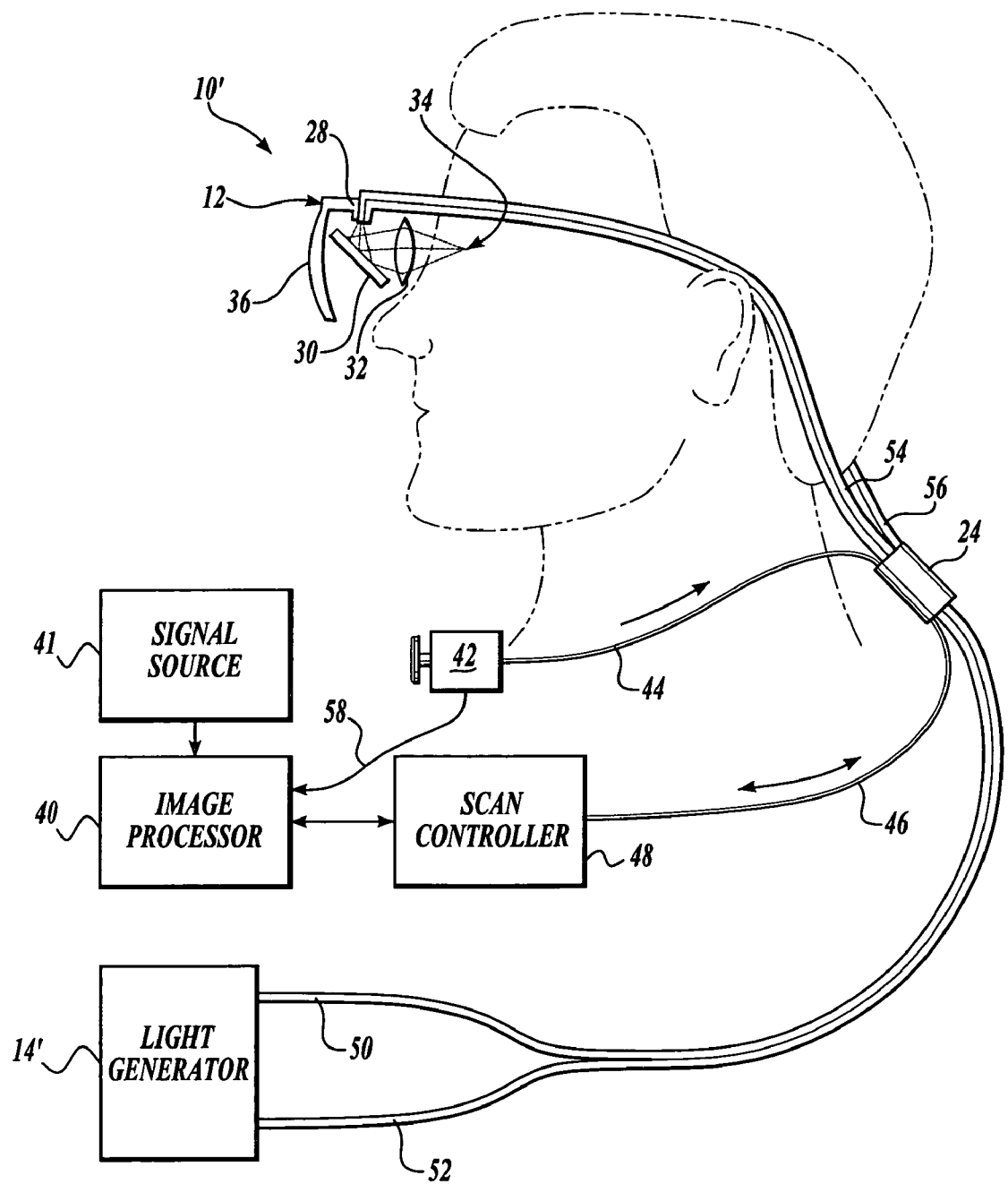
FIG. 2 depicts an alternative embodiment of the invention for visible laser diode single-photon excitation.

FIG. 2 illustrates another embodiment of system 10' having similar elements identified by the same reference numerals in FIG. 1. The primary difference in the embodiment shown in FIG. 2 is pulsed light energy generator 14'. In FIG. 2, pulsed light energy generator 14' is comprised of one or more laser diodes that each produce light energy in the near UV to visible wavelengths. UV and violet (350-420 nm) laser diodes recently introduced by Nichia Corporation of Tokushima, Japan may be useful in embodiments of the present invention that are completely wearable and portable. Laser diodes producing light energy of greater than 20 mW optical power at 405±10 nm were introduced by Nichia Corporation in 2000 and laser diodes producing light energy at 370-380 nm were introduced in 2002. UV and violet laser diodes have enough energy per photon to directly stimulate the retinal neurons. Longer wavelength green and red solid state and laser diodes are commonplace and may provide the required laser power for the direct modulation of retinal neurons.

Notably, system 10' illustrated in FIG. 2 does not include electronic shutter and modulator 16 and group velocity dispersion compensator 18. This is because the laser diodes in pulsed light energy generator 14' are directly modulated by image processor 40. The laser diodes may be directly connected (i.e., "pigtailed") to optical fibers 50, 52 that communicate the light energy to the left and right eyes, respectively. Exemplary devices for pigtailing to optical fiber are available from Micro Laser Systems of Garden Grove, Calif. The optical fibers 50, 52 are connected to optical fibers 54, 56 via the cabling disconnect 24. For purposes of redundancy or safety, multiple laser diodes of lower intensity may be coupled to optical fibers 50, 52. The output of the two or more laser diodes can be combined by either polarization or dichroic beam splitters before coupling to the optical fiber. Since the laser modulation produces pulses of relatively long duration for single-photon stimulation versus multiphoton excitation, compensation for group velocity dispersion is not needed.

Camera 42 in FIG. 2 is also shown with an alternative direct wiring 58 to image processor 40, instead of using the path comprised of wires 44, 46, and scan controller 48. Wiring 58, and other wiring discussed herein, may also be accomplished using wireless signal communication, where it is technologically feasible and desired.

Systems 10 and 10' in FIGS. 1 and 2 depict a wearable neuro-stimulating prosthesis providing single or multi-photon laser excitation using either diode-based or femtosecond-pulsed lasers. Both single and multi-photon lasers discussed herein can use the same optical fiber, such as a singlemode optical fiber, for the near-infrared wavelengths. They can also use the same mirrors and fiber scanners, and the same delivery optics, for directing the light energy to the retinal neurons.

Cabling disconnect 24 depicted in FIGS. 1 and 2 permits a user to switch from a larger femtosecond-pulsed NIR laser system at home or at work to a portable, single-photon laser system (and visa versa). In that regard, cabling disconnect 24 is configured to provide the same interface to the optical fibers extending from the laser sources of both system configurations.

Figure 3:
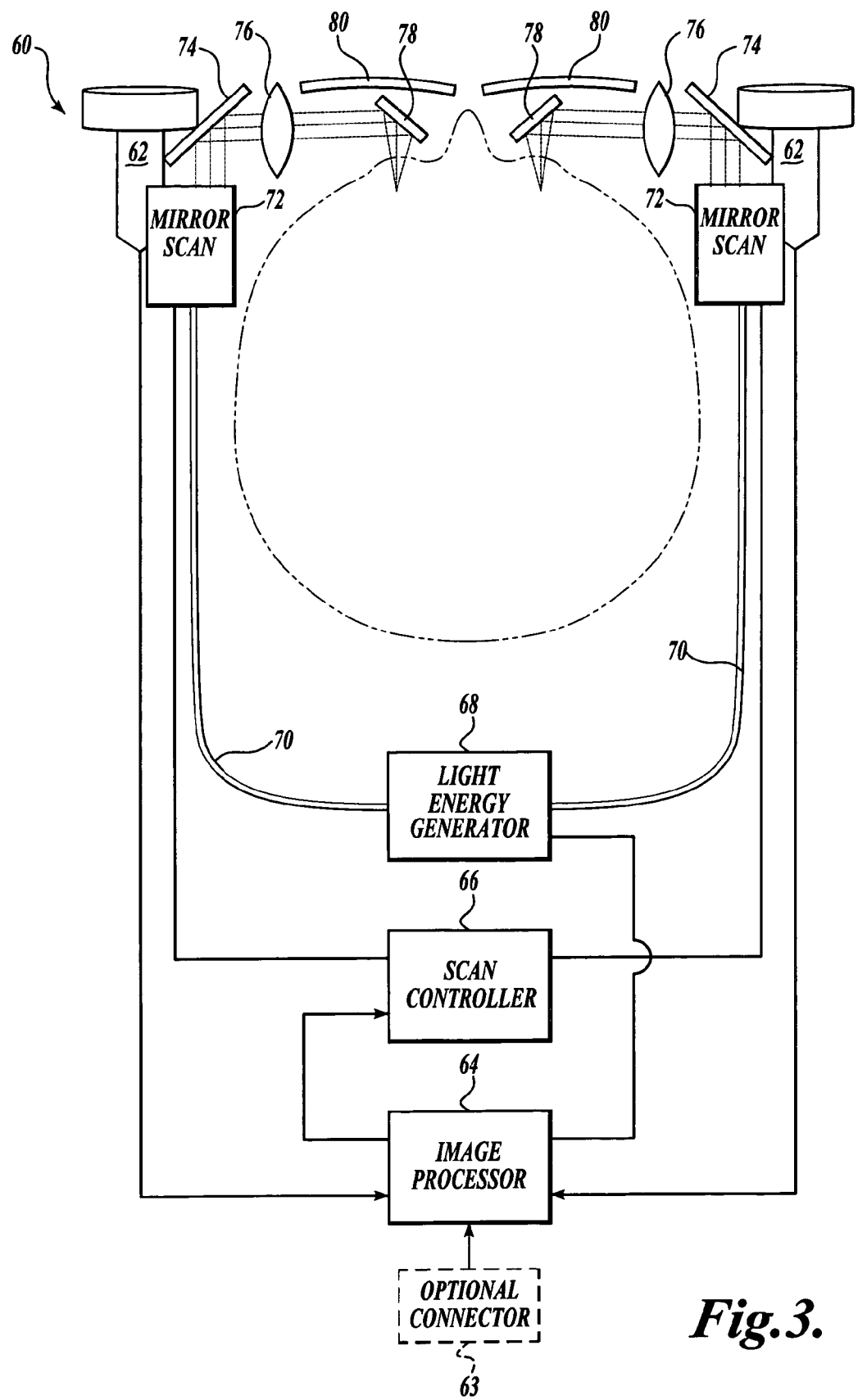
FIG. 3 illustrates another embodiment of a visual prosthesis of the invention that uses high-power UV or visible light emitting diodes (LEDs) to produce the stimulating light energy.

FIG. 3 illustrates another embodiment of a visual prosthesis of the invention that uses high-power UV or visible light emitting diodes (LEDs) to produce the stimulating light energy. In FIG. 3, system 60 is shown from a top view, including a top view of the head of the wearer of the headpiece. Attached to the headpiece are cameras 62 connected to an image processor 64. Electrical signals from image processor 64 are amplified and modified by a scan controller 66. Image processor 64 also controls a light energy generator 68, which in this embodiment is comprised of high-power visible LEDs. The light energy produced by the light energy generator 68 is communicated via optical fibers 70 to two-dimensional X-Y mirror scan systems 72. The X-Y mirror scan systems include piezoelectric elements that cause mirrors in mirror scan systems 72 to direct the light energy to form a scanned pattern of light intensities on the user's retina. Alternative actuation methods are employed for generating X-Y mirror scanning in resonance and non-resonance motion by manufacturers of retinal scanning displays (Microvision Inc., Bothell, Wash.) and optical switching devices (MEMS Optical Inc., Huntsville, Ala.), respectively. An alternative method for vector or random-access scanning a laser beam is to use two orthogonally mounted acousto-optic deflectors, (Iyer et al. (2002) *Proc. 2nd Annual Joint EMBS/BMES Conference*, Houston, Tex., Oct. 23-26, 2002, 2101-2). As depicted in FIG. 3, the light energy is delivered to the user via mirrors 74, scan lenses 76, and mirror or beam splitters 78. Spectacle lens 80 may be attached to the front of the headpiece to darken the user's eyes and/or add aesthetic effect to the headpiece.

Because system 60 uses LEDs for generating the light energy, the system is extremely robust and can be battery powered and completely portable. The system is also produced at a much lower cost. For example, Cree Inc., (Durham, N.C.) manufactures high-brightness edge-emitting LEDs for retinal-scanning display applications for Microvision Inc. (Bothell, Wash.), and Nichia Corporation (Tokyo, Japan) manufactures high-power UV LEDs that have a 100 mW source producing 380 nm light. Most all LEDs are extremely durable and have long lifetimes (greater than 50,000 hours).

The source size for LEDs is large enough to have more than a single optical fiber coupled to the emitter. To improve coupling efficiency, the fibers can have a larger core diameter than the singlemode optical fibers depicted in FIGS. 1 and 2.

While system 60 may be lower in cost, presently available components render it unable to produce images of highest resolution and brightness as compared to the system 10 in FIGS. 1 and 2. The larger the size of the fiber optic source, the larger the imaged spot will be at the retinal neurons. Hence, LED-based system 60 may have a lower visual resolution and/or image brightness that is perceived.

Cameras 62 are shown mounted on the spectacle frame and are capable of producing still or continuous video images. Suitable embodiments of the cameras include "lipstick-style" CCD (obtainable from ELMO USA, Painview, N.Y.) or "sugar-cube" CMOS camera heads (obtainable from IC Media Corp., San Jose, Calif.). One or more cameras may alternatively be mounted on the body of the user, as shown in FIGS. 1 and 2. Image processor 64 receives the image signal from cameras 62 and modulates the light energy produced by the LEDs in light energy generator 68. Image processor 64 also controls the drive signals from can controller 66 so that the X-Y scanner is synchronized with the light energy modulation. As with system 10 depicted in FIGS. 1 and 2, the spatially and intensity-modulated photostimulation generates two-dimensional images that are perceived by the brain, thus mimicking a functional human retina. Further, as with system 10 in FIGS. 1 and 2, system 60 may use fiber-scanning technology to produce the scanned image, in place of mirror scanning system 72 shown in FIG. 3.

Compared to system 10, system 60 is less efficient in terms of photostimulation but is lower in cost and is more durable. Also, as noted above, single photon LED neuro-stimulation may use larger core optical fibers, producing larger light spots (and consequent lower resolution images) at the retina. Thus, optical fibers 70 may be multimodal, as opposed to the singlemode fibers depicted in FIGS. 1 and 2.

In the systems depicted in FIGS. 2 and 3, the optical and electronic components may be carried in either a waist belt, backpack, vest with pockets, or otherwise clipped or strapped to the body. The portable systems will be powered by batteries. An exemplary wearable computer that may be used as image processor 64 is available from Xybernaut of Fairfax, Va.

In all embodiments of the invention, the image that is processed and scanned on the user's retina may come from a wide variety of sources, including video or still frame cameras that capture visible and/or non-visible wavelength light. The sources may also include computer-generated signals, television signals, video tape, DVD, etc. (for example, block 41 in FIGS. 1 and 2). FIG. 3 further depicts an optional connection 63 to image processor 64 for connecting an alternative image source (in place of or in addition to cameras 62).

Figure 4:
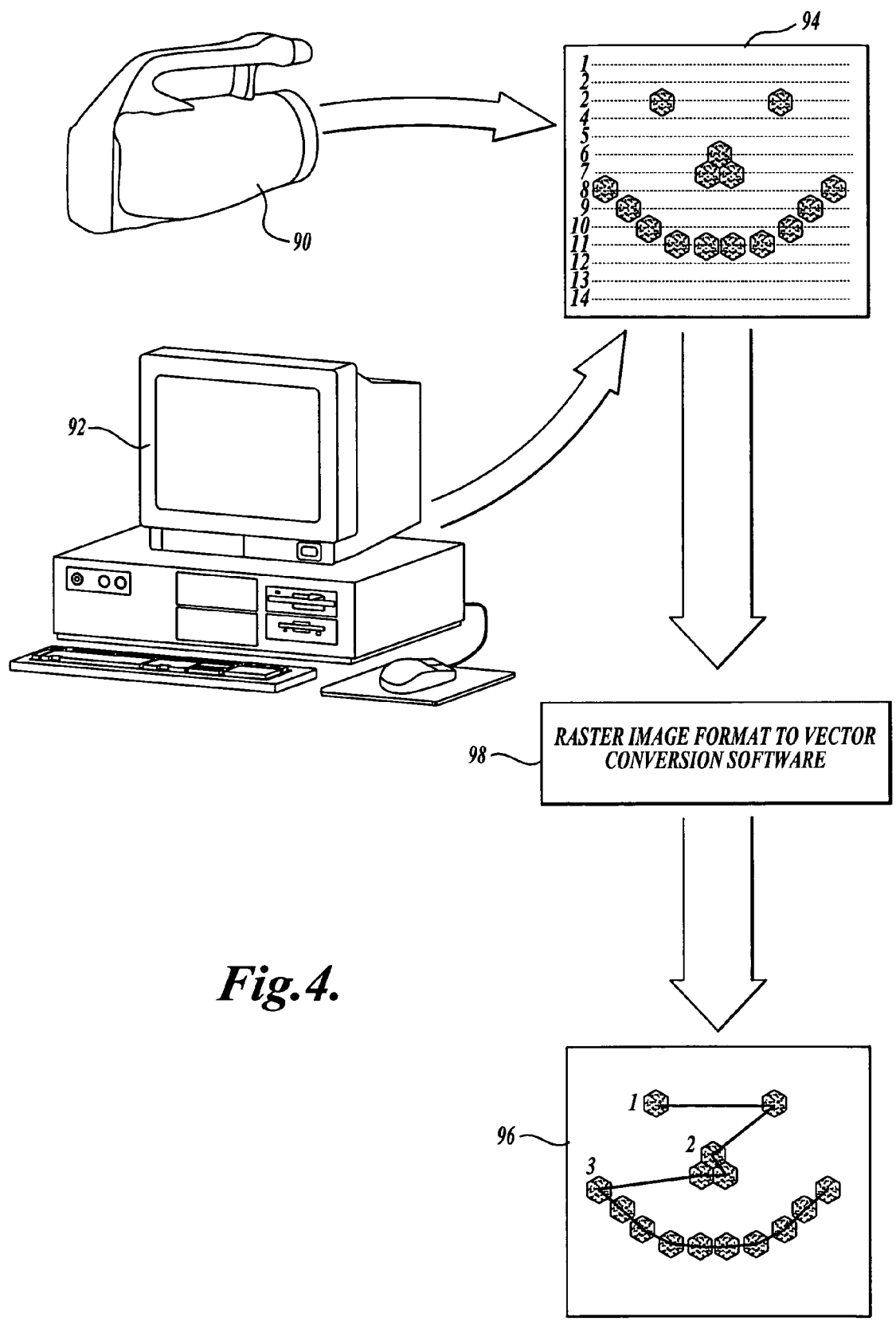
FIG. 4 depicts a means to increase the laser energy per image projected onto the retina by conversion of the scanned image from the standard raster to a vector graphics format. The scan distance is significantly reduced using the vector graphics format (about 90% in the example shown), allowing more light exposure per pixel assuming constant optical power of the illumination beam.

The most optically-efficient means for scanning an image to the retina is to convert the image source from a raster format to a vector graphics format, as shown in FIG. 4. Typically, video cameras 90 and electronic display devices 92 use raster scanning format 94, where the scan covers a fixed area and pixels of the image are either turned on or off with graded intensity and optionally color. Since photon energy is being used to modulate neural activity in the retina, the most efficient use of the stimulating light is important. Otherwise, the eye can warm up due to excessive optical radiation, possible damaging the melanin-containing retinal pigmented epithelium. Vector scanning 96 either drives a fiber scan system or mirror scan system to follow a path in X-Y space, similar to how an image is hand-drawn. As a component to a vision prosthesis, the image source will be reduced in detail by first enhancing edges of all objects or segmented objects and then thresholding the color or grayscale image into binary (On or Off) before converting the image to a vector graphics format and possible rescaling (Vargas-Martin & Peli (2001) *Soc. Information Display Tech. Digest* 32:602, FIG. 1). Software 98 is commercial available for making the conversion from raster to vector graphics format (e.g., Algolab Photo Vector, Algolab, Ontario, Canada).

Fiber scanner 28 may be connected to wearable headset 12 in a cantilevered configuration and, as noted above, may be driven by one or more piezoelectric actuators in either a resonant raster scan or a X-Y addressable vector scan. A laser-diode-based, wearable fiber-scanned display has been developed for low vision applications (Seibel et al. (2002) *Soc. Information Display Tech. Digest* 33(1):338-341). Alternative retinal scanning display using resonant mirror scanning has been validated as a low vision aid (Kleweno et al. (2001) *J. Rehab. Res. Dev.* 38(4):431-42). A femtosecond-pulsed NIR fiber-scanned system that is wearable by an animal has been developed (Helmchen et al. (2001) *Neuron* 31:903-12). Lens 32 or lens system may be suitably adjusted for the prescription or eye refraction of the user.

When using lower-power UV or visible laser diodes (that are directly modulated as discussed above), the output of two or more laser diodes may be combined using a polarization cube beam splitter or combiner. The output of a laser diode may be communicated via a polarization-preserving singlemode optical fiber through a collimating lens into the cube beam splitter or combiner. Similarly, the output of another laser diode may be communicated via a polarization-preserving singlemode optical fiber through another collimating lens into the cube beam splitter or combiner. The combined output of the laser diodes is then directed from the cube beam splitter or combiner through a collimating lens into a singlemode optical fiber (see products of OZ Optics Corp., Carp, Ontario). The combined beams from the laser diodes may have mixed parallel and perpendicular linear polarizations that may double the optical power output of the system. Using two or more laser diodes, in this respect, may also provide redundancy in case of failure of a laser diode. In the above described system, a dichroic beam splitter may be used in place of the cube beam splitter or combiner. A fiberoptic combiner may be used as well (see Canadian Instrumentation & Research Ltd., Burlington, Ontario; SIFAM Fibre Optics Ltd., Devon, UK).

Representative examples of apparatus that may be adapted for use in the practice of the present invention to scan beams of light energy onto a user's retina, and thereby modulate neural activity in the retina, are disclosed in U.S. Pat. Nos. 5,355,181; 5,467,104; 5,596,339; 5,727,098; and 6,046,720, the disclosures of which are incorporated herein by reference. It is also contemplated within the scope of the present invention to use the visual prosthesis to stimulate neurons other than those in the retina. For instance, the imaging system of the invention may produce electric signals that modulate neural activity relating to other senses, such as hearing, smell, taste, or touch, thus producing an artificially-formed sense for the user of the prosthesis.

Figure 5:
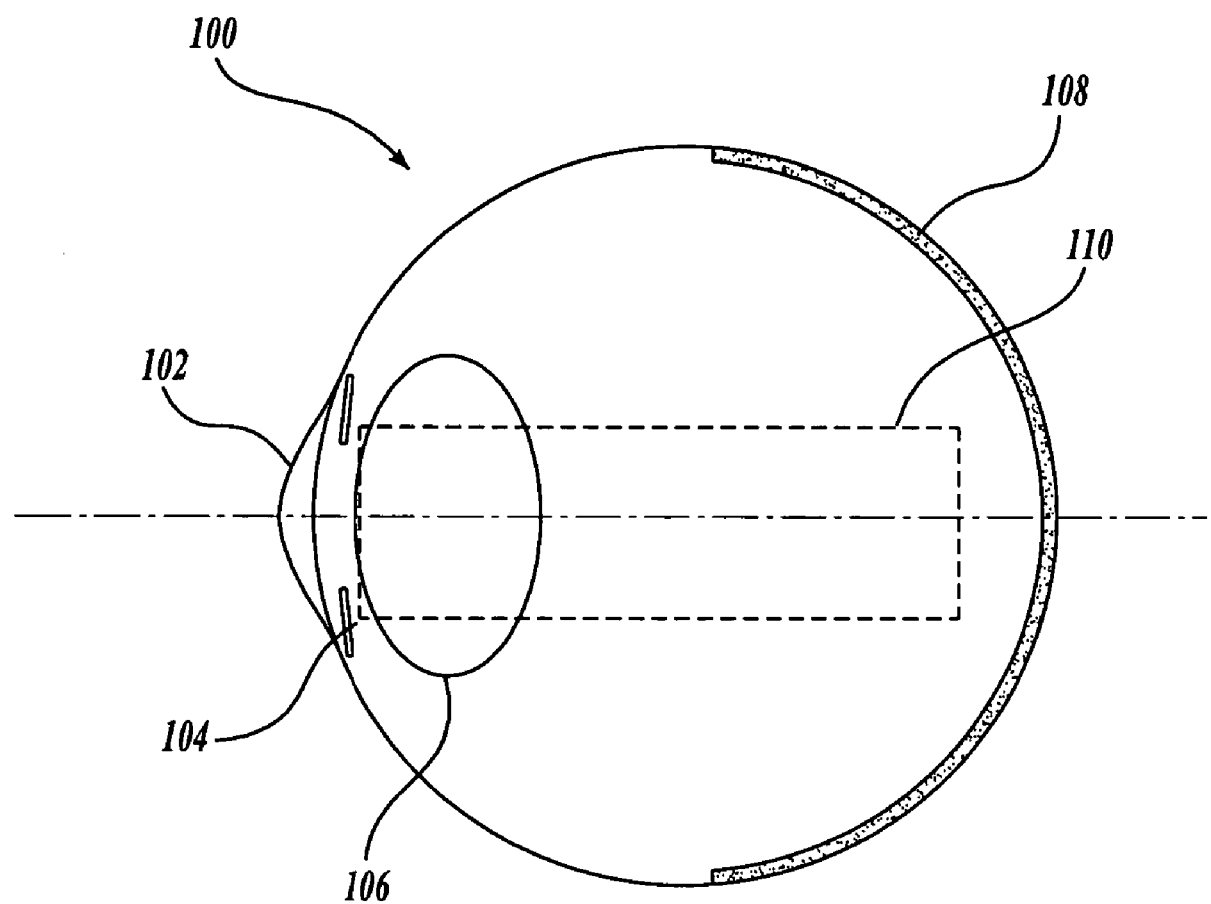
FIG. 5 depicts an alternative means of increasing laser energy density to the retina by having an intraocular lens (IOL) to more efficiently focus the laser energy at the retinal neurons.

To produce the smallest optical spot size-and thus improve image resolution-in the user's retina, the present invention further contemplates fitting the user with a contact lens or an implanted intraocular lens (IOL) that is customized for this application. FIG. 5 shows a representation of a mammalian eye 100 including the cornea 102, the iris 104 (dilated), a crystalline lens 106, the retina 108, and an implanted IOL 110. The natural pupil diameter, when less than about 2.7 mm, limits the numerical aperture (NA) or focusing ability of eye 100, while aberrations in the cornea 102 and crystalline lens 106 limit the NA (resulting in reduced resolution and contrast of the perceived image) when the pupil is larger than about 2.7 mm. A large NA benefits direct stimulation of retinal neurons using the system and methods of the invention by producing smaller spots of irradiation on retina 108. Means to increase the NA of eye 100 include increasing the pupil diameter (e.g., dilation) and correcting for optical aberrations in eye 100 with either a custom contact lens or IOL 110 (e.g., a custom GRadient INdex optical lens to replace natural crystalline lens 106). Such customized lenses can correct for higher order aberrations of the user's eyes at the wavelengths of the pulsed light energy generator (e.g., the laser) and the degree of collimation of the optical beam(s), and also reduce scatter and absorption. Anti-reflection coatings may be applied to the custom lens surfaces to reduce unwanted surface reflections. In an eye 100 whose retina 108 is completely unresponsive to light, it may be desirable to completely remove iris 104 and crystalline lens 106 and replace them with a custom scan lens system in order to increase the NA of the incoming light energy that is being focused directly on the neurons of retina 108, especially for the high spatial density of retinal neurons near the foveal and macular regions. In addition, permanent changes to cornea 102 may include laser sculpting for optimal focus of the wavelength and beam quality of the light energy used in the system and methods of the invention.

If UV light is used for the stimulation of the retinal neurons, then the user will require a standard IOL replacement since the natural crystalline lens does not transmit efficiently in the UV. Standard IOL replacements may also transmit infrared light efficiently. However, they may not be optimized for the laser wavelengths used for multi-photon photostimulation of retinal neurons so a custom IOL may be desirable.

Thus, in some embodiments of the invention crystalline lens 106 from one or both eyes of a mammalian subject may be removed and replaced with artificial lens 110 that is better adapted to focus light energy onto retina 108. The ability to design and make a custom contact lens for enhanced vision has been recently demonstrated (Guirao et al. (2001) *J. Opt. Soc. Am. A. Opt. Image Sci. Vis.* 18(5):1003-15, incorporated by reference herein). Accordingly, a customized contact lens or intraocular lens (IOL) may be designed to improve the efficiency of the optical radiation delivered by the visual prosthesis. Since both macular degeneration and cataracts are age-related ocular diseases, the IOL replacement of the crystalline lens for cataracts may coincide with the implementation of the visual prosthesis of the present invention. Customized lenses may also be configured to correct for higher-order aberrations in the user's eyes. In this manner, the focal spot at the user's retinal neurons may be optimized (see discussion of customized contact lenses in Guirao et al. (2001) *J. Opt. Soc. Am. A. Opt. Image Sci. Vis.* 18(5):1003-15). For example, IOL lens implants are being designed with adaptive optics for user's to compensate for natural lens aberrations (Hogan et al. (2003) *Biophotonics Intl.* August 2003, p. 34-7). This concept may be extended to IR for efficient photostimulation.

In age-related macular degeneration, the natural photoreceptors in the macular region of the eye either partially or fully fail to function. However, photoreceptors in the peripheral regions may continue to function properly. Accordingly, the higher-power photostimulation provided by the visual prosthesis of the invention is directed to the macular region of the eye. Light energy directed to the periphery of the macula may originate with low-power visual laser light sources to stimulate the functional photoreceptors, while the higher power laser is focused on the macular region for direct modulation of retinal neural activity. The visible lasers may include the combined beams of red, green, and blue wavelength ranges to provide full color to the functional photoreceptors, while one of these lasers or a femtosecond-pulsed NIR laser provides the laser power for stimulating the region of non-functioning photoreceptors. Thus, the neural stimulators may be composed of natural or artificial elements. Particularly in the case of a user having a region of functional photoreceptors, the option of gaze tracking or eye-movement monitoring may be desirable. In the simplest case, only when the user's straight-ahead gaze is aligned with the optical axis of the device will photostimulation of the retinal neurons occur. Optical sensors or cameras are typically used for gaze tracking or more simply gaze-alignment monitoring, such as using the reflected red-pupil signal that occurs when the gaze is roughly aligned with a white light source, often seen in flash photographs.

The natural eye of a human has a numerical aperture (NA) of approximately 0.2 or less for a pupil of 5 to 6 mm in diameter. In order to improve resolution of scanned images, the retinal neurons may be stimulated by light energy directed through an implanted intraocular lens of higher NA, as described above. In that regard, as noted above, it is contemplated to replace the entire optics of the eye with a replacement that functions as a high NA objective for the light energy stimulation of the retinal neurons. The eye replacement may be designed to look like a natural iris and sclera, to be aesthetically pleasing for persons interacting with the blind person. The high NA replacement in this regard may be on the order of 0.7, i.e., at least three to four times the NA of the natural eye. Artificially raising the NA of the eye may significantly increase the efficiency of multiphoton excitation or optoporation at the retina because the probability of two-photon excitation is proportional to the fourth power of NA (Denk et al. (1990) *Science* 248: 73-6.)

As an alternative to scanning light energy onto the retina, a high-intensity beam of light may be expanded to fill a spatial light modulator, such as liquid crystal on silicon chip (LCOS) or a Microelectromechanical system such as the Digital Multimirror Device (DMD, Texas Instruments Inc.). Instead of having to retrace the entire scan every frame, the pixel-array device modulates the intensity of each pixel in the display at the same time, which is updated every frame. The spatial light modulation creating an image on the surface of the pixel-array device is re-imaged onto the retina to form the image stimulus. In this alternative method, the optical beam is not scanned and illumination from several high-brightness LED's may provide sufficient optical power for modulating neural activity. Since all pixels in each image are presented simultaneously using the DMD or LCOS pixel array chips, the preferred method of illumination using the LED light source(s) will be in a pulsed mode. Pulsing LEDs can provide much higher peak powers than continuous operation of LEDs.

Figure 6:
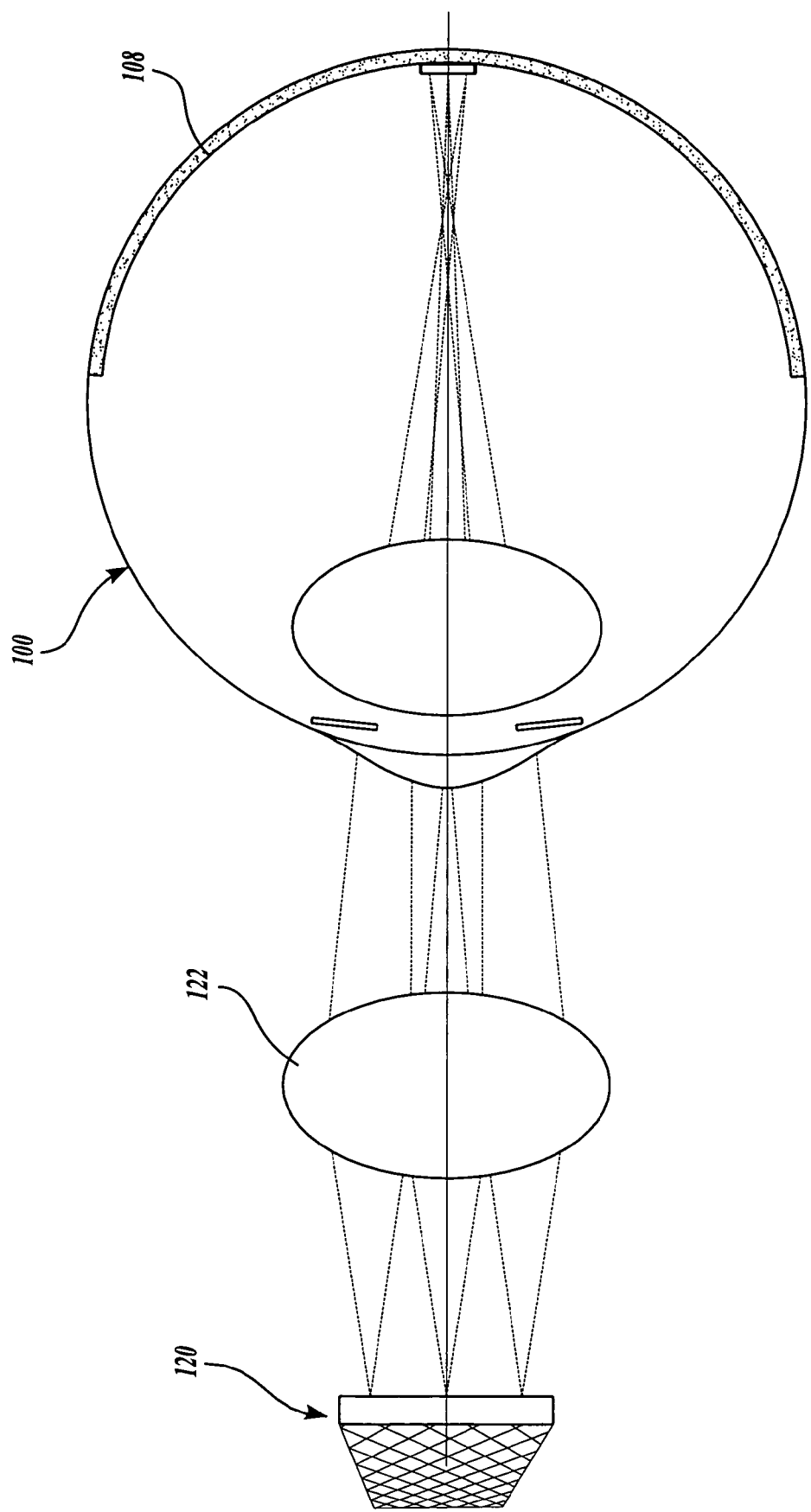
FIG. 6 depicts an array of micro light emitting diodes (micro-LEDs) or micro-lasers that would be head-mounted and the image of the light sources be projected onto the retina. Optical rays from three sources are shown. The array of light sources may be replaced with a spatial light modulator.

As shown in FIG. 6, an array of light sources 120 (e.g., a two-dimensional array of superbright LEDs, reviewed in Boas (2003) *Biophotonics Intl.*, p. 27-28) that are individually-addressable and directly-modulateable in light output, which can be re-imaged and minified directly onto the retinal neurons of the eye, may simply replace the planar spatial light modulators (LCOS and DMD chips). Because each light source is individually addressable, complex patterns can be projected into eye 100. Projection lens 122 (e.g., with ¼ magnifying power) minifies an image of the array of light sources 120 in order to project a high-resolution pattern of irradiation on retina 108. The advantage of having an array of light sources is that each light source can stimulate the same region of the retina for the duration of the frame, which is usually 33 ms to 10 ms for video display frame rates of 30 to 60 Hz. For this reason, scanning and sweeping the light onto the retinal neurons across the entire field of view of the image is not required. However, image resolution (pixel number) is limited by the number of light sources in the array. To increase the number of photo-excited pixels, the array of light sources or the array of optical beams from a microlens array can be scanned.

The following examples merely illustrate the best mode now contemplated for practicing the invention, but should not be construed to limit the invention.

EXAMPLE 1

This Example describes the optoporation of ganglion cells in embryonic chicken retinas using near-infrared irradiation.

Extraction of Chicken Embryos: Embryonic chicken retinal explants were used for all experiments. Eggs were kept in an incubator until immediately prior to use. The contents of each egg were transferred to a Petri dish where the embryo was separated from the rest of the egg contents using sterile forceps. The embryo was then transferred to a separate dish containing Hank's Buffered Saline Solution (HBSS). During the separation and transfer stages, the embryo was shoveled about, rather than pinched with the forceps. This process was repeated until the proper number of embryos had been collected.

Once all of the embryos had been extracted, they were viewed under a dissection scope to determine their stage using a staging manual. The stage of the embryos varied from experiment to experiment but were always in the range of stage 29 to 41.

Dissection of Embryonic Chicken Retinas: Direct contact with the eye was minimized during dissection in order to avoid accidentally damaging the eye. Once the eyes were separated from the rest of the embryo, they were transferred to a new Petri dish containing HBSS. Once the eyes were transferred to a new dish, extraction of the retinas followed. Dissection of the eye itself began with the removal of the cornea and the lens. The eye was then splayed out to ease separation of the retina from the retinal pigmented epithilium (RPE). The act of splaying the eye caused parts of the retina to detach from the RPE. These initial tears provided space to hold the eye immobile while only pinching the RPE and outer layers. While the eye was held immobile, the retina was gently teased away from the RPE by sliding a set of forceps between the retina and the RPE (not by pinching the retina and pulling it). The retinas were then transferred to a third dish containing HBSS. The retinas were quartered using forceps. Each quarter was then transferred to a coverslip chamber. Retinas were stored at 37° C. for a maximum of 5 hours in 0.5 ml of HBSS.

Near-Infrared Irradiation of Retinas: All experiments were performed at the University of Washington's Keck Imaging Center. Cell membranes were targeted using a confocal laser scanning microscope (TCS SP/MP, Leica Microsystems AG, Wetzlar, Germany). The Leica TCS is an inverted microscope. Two-photon 2P optoporation experiments were performed using a Spectra-Physics Tsunami Ti:Sapphire laser. The laser has a tuning range of 720 nm to 850 nm, a maximum power at the sample of 120 mW, a pulse width of 1.3 ps, and a repetition rate of 82 MHz. 2P experiments were performed using near-infrared (NIR) wavelengths in the range of 720-810 nm.

Immediately before the beginning of each experiment, green-fluorescent protein (GFP) plasmid DNA (Qiagen, Wetzlar, Germany) was added to the HBSS to a final concentration of 25 micrograms/ml.

Prior to irradiation with the 2P laser, images of the cells were obtained using Differential Interference Contrast (DIC) imaging. DIC images were collected using reflected light at 488 nm from an Argon laser. The DIC images were used to bring the edge of cell membranes into focus. Once a focused DIC image was obtained, an advanced time lapse series was started. This series consisted of a DIC image taken with the 488 nm laser, then a bleach experiment with the 2P laser (irradiation time ~500 ms), then another DIC image with the 488 nm laser. The bleach experiment on the Leica TCS system consists of an interactive dialogue box where the user can pick a specific point for the Leica Software to park the beam for a specified duration in time. Points in the middle of the retinal explant were targeted.

Following irradiation, the retinas were incubated rolling for 18 hours at 37° C. in tissue culture media (20 ml 5× DMEM F-12, 2 ml 30% Glucose, 1.5 ml 7.5% NaHCO$_3$, 0.5 ml 1 M HEPES, 65 ml sterile water, 10 ml Hormone Supplement, 1 ml FBS, and 1 ml of Penn/Strep). Retinas where then fixed using 4% paraformaldehyde for 1 hour at room temperature. The tissue was then rinsed twice for 5 minutes with Phosphate Buffered Saline (PBS). Following the second rinsing, the tissue was mounted on microscope slides using either Fluoromount or Glycerol. The slides were then stored at 4° C. until checked for fluorescence.

Fluorescence Microscopy: Tissue fluorescence was determined using a fluorescence microscope. Images were collected on a Macintosh computer using Spot and edited using Adobe Photoshop. The transfected cells were determined to be ganglion cells by the cell morphology. Based on fluorescence microscopy, the overall transfection efficiency was determined to be 42%.

While the preferred embodiment of the invention has been illustrated and described, it will be appreciated that various changes can be made therein without departing from the spirit and scope of the invention.

The invention claimed is:

1. A vision prosthesis system, comprising a light energy generator operably connected to a wearable head piece comprising a device for directing light energy produced by the light energy generator onto a mammalian retina, wherein the light energy generator is tuned to emit light energy of sufficient power to directly modulate neural activity in the retina in neurons other than rods and cones, and wherein the light energy generator is a light source selected form the group consisting of a femtosecond-pulsed light source and a picosecond-pulsed light source.

2. The system of claim 1, wherein the light energy generator is tuned to emit visible light energy.

3. The system of claim 1, wherein the light energy generator is tuned to emit ultraviolet light energy.

4. The system of claim 1, wherein the light energy generator is tuned to emit infrared light energy.

5. The system of claim 1, wherein the light energy generator is selected from the group consisting of a laser, a laser diode, a mercury arc lamp, and a light-emitting diode.

6. The system of claim 1, wherein the device for directing light energy onto the mammalian retina is a scanner.

7. The system of claim 6, wherein the scanner is selected from the group consisting of a fiber optic scanner, a mirror scanner, and an acousto-optical deflector.

8. The system of claim 6, wherein the scanner is a non-resonant scanner.

9. The system of claim 6 further comprising an image source operably connected to the scanner.

10. The system of claim 9, wherein the image source is a camera.

11. The system of claim 1, wherein the system is controlled by a computer.

12. A method for modulating neural activity in the retina of a mammalian eye, comprising the step of directing light energy produced by a light energy generator onto a mammalian retina to directly modulate the activity of retinal neurons other than rods and cones, and wherein the eye comprises an artificial lens, the method further comprising the step of directing light energy through the artificial lens to focus the light energy onto the retina.

13. The method of claim 12, further comprising generating a pattern of nerve impulses within the retina to construct a visual image.

14. The method of claim 12, wherein the step of directing light energy produced by a light energy generator onto a mammalian retina comprises directing light energy produced by a light energy generator selected from the group consisting of a laser, a laser diode, a mercury arc lamp, and a light-emitting diode onto a mammalian retina.

15. The method of claim 12, wherein the step of directing light energy produced by a light energy generator onto a mammalian retina comprises directing visible light energy onto the mammalian retina.

16. The method of claim 12, wherein the step of directing light energy produced by a light energy generator onto a mammalian retina comprises directing ultraviolet light energy onto the mammalian retina.

17. The method of claim 12, wherein the step of directing light energy produced by a light energy generator onto a mammalian retina comprises scanning the light energy onto the mammalian retina in raster format.

18. The method of claim 12, wherein the step of directing light energy produced by a light energy generator onto a mammalian retina comprises directing light energy scanned in vector graphics format onto the mammalian retina.

* * * * *

UNITED STATES PATENT AND TRADEMARK OFFICE
CERTIFICATE OF CORRECTION

PATENT NO. : 7,311,723 B2 Page 1 of 1
APPLICATION NO. : 10/888428
DATED : December 25, 2007
INVENTOR(S) : E. J. Seibel et al.

It is certified that error appears in the above-identified patent and that said Letters Patent is hereby corrected as shown below:

| COLUMN | LINE | ERROR |
|---|---|---|
| 18 (Claim 1, line 8) | 2 | "form" should read --from-- |
| 18 (Claim 1, line 9) | 3 | "a femtosecond-pulsed" should read --the femtosecond-pulsed-- |

Signed and Sealed this

Third Day of November, 2009

David J. Kappos
*Director of the United States Patent and Trademark Office*